United States Patent [19]
Lancia et al.

[11] 4,126,857
[45] Nov. 21, 1978

[54] PROBE-TYPE LIQUID DETECTOR

[75] Inventors: Frederick N. Lancia, Columbus; Albert O. Kesterson, Worthington, both of Ohio

[73] Assignee: Liebert Corporation, Columbus, Ohio

[21] Appl. No.: 814,292

[22] Filed: Jul. 11, 1977

[51] Int. Cl.² .............................................. G08B 21/00
[52] U.S. Cl. ...................................... 340/620; 338/35; 340/605
[58] Field of Search ................... 340/235, 244 C, 242; 338/34, 35, 229

[56] References Cited

U.S. PATENT DOCUMENTS

| | | | |
|---|---|---|---|
| 3,279,379 | 10/1966 | Klyce | 340/244 C |
| 3,399,399 | 8/1968 | Apfelbaum | 340/244 C |
| 3,523,244 | 8/1970 | Goodman et al. | 338/35 X |
| 3,582,930 | 6/1971 | Wiley | 340/240 C |
| 3,696,360 | 10/1972 | Gajewski | 340/235 |
| 3,757,316 | 9/1973 | Fiorenzo | 340/243 |

Primary Examiner—John W. Caldwell, Sr.
Assistant Examiner—Daniel Myer
Attorney, Agent, or Firm—Gerald L. Smith

[57] ABSTRACT

Apparatus and system for monitoring sites for the presence of moisture or the collection of conductive liquids. Two housings are utilized with the apparatus to facilitate user convenience. A first of these housings, mounted at a location selected for easy access by the user, retains manually actuated switching, alarm components and batteries. This housing is electrically coupled with a second, smaller housing serving to encapsulate solid-state switching logic components and moisture detecting probes. Spurious R.F. noise is avoided within the system through the positioning of this solid state switching at the second housing in close adjacency with the probes. The probes are formed of a base material, one surface portion of which is covered with a noble metal, such as platinum. The remaining surfaces of the base are permitted to develop, in situ, a surface oxide which is immune to galvanic corrosive participation.

16 Claims, 7 Drawing Figures

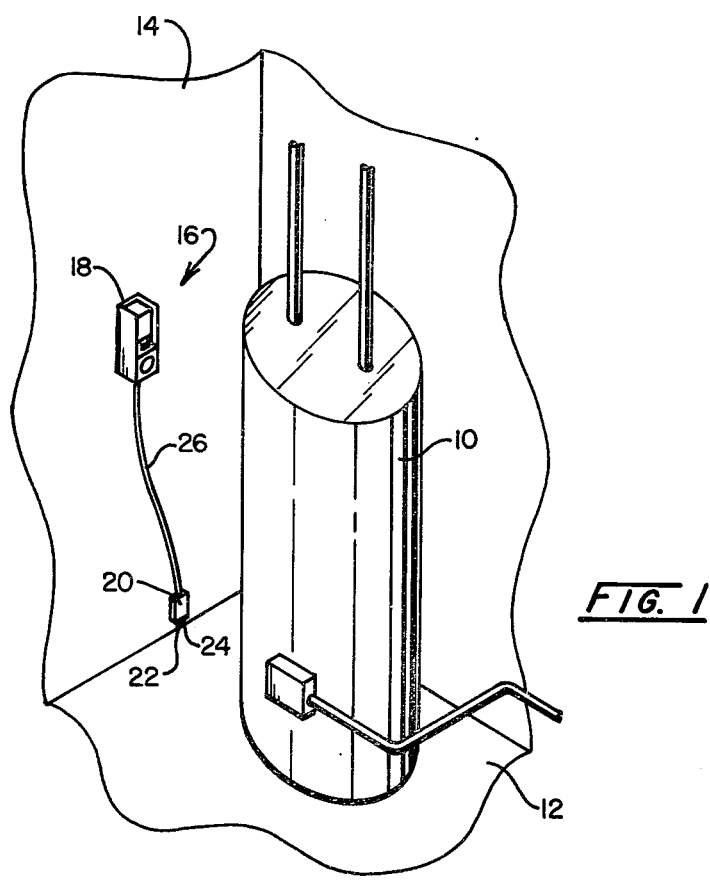
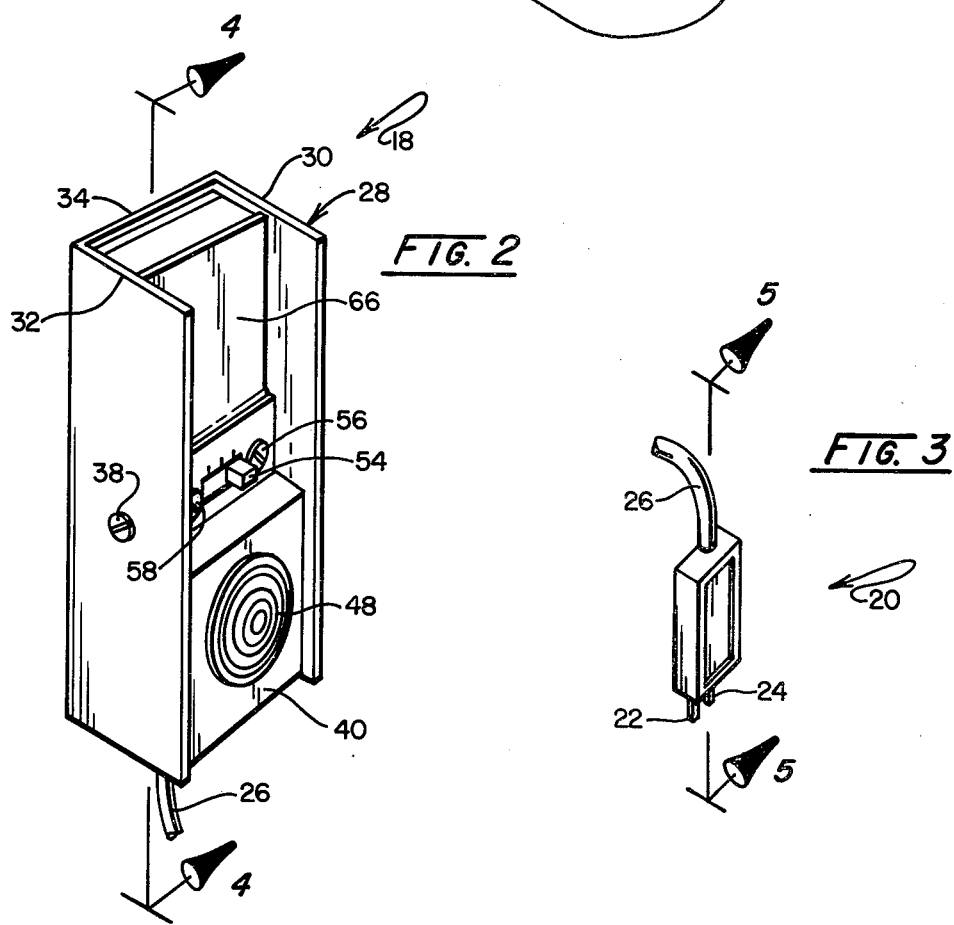

PROBE-TYPE LIQUID DETECTOR

BACKGROUND

Liquid level or film detection devices are found to have broad utility in industrial as well as domestic application. In one aspect, the devices exhibit important utility in monitoring predefined areas for the detection of excursions in liquid conveying systems. As an example, the rigid humidity controls necessarily present in many industrial environments, e.g. computer rooms and the like, require the presence of water conveying conduits which conventionally are positioned in a subfloor enclosure which also serves to retain an extensive concentration of electrical conduiting and the like. Ruptures of pressurized water lines in such environments and others can result in extensive damage to equipment, including important data retention componemts, in the absence of a prompt and adequate warning of excursions at the incipient stage of any given failure. In domestic applications, a need has been recognized for an inexpensive, very easily installed device which is operative to detect and provide a form of alarm upon the incidence of sudden or progressive failure in water retaining and/or conveying implements such as boilers, water heaters, sump pumps, clogged air conditioning condensate drains, dishwashers, clothes washers, as well as the incidence of flood water, foundation leaks or sewer back-up conditions. Similarly, the devices find utility in marine use, with respect to boat holds, engine compartment flooding, bilge pump failures and the like. Consumer market as well as industrial market acceptance of devices for providing incipient state warning of water system failure requires that such devices exhibit high standards of reliability coupled with an extended term performance capability. In the latter regard, owners in the consumer field cannot be expected to frequently inspect and test all components within a water or moisture excursion monitoring system. Only the most basic and simple inspection routines can be expected of the domestic user. Accordingly, incipient failure warning devices should exhibit designs permitting highly convenient access to the use for such routine maintenance procedures as battery testing and/or replacement as well as testing of any audible or perceptible alarm components. Usually, however, the locations or sites at which testing devices are located necessarily are remote from the user, leading to the neglect of maintenance procedures. Techniques wherein more or less lengthy electrical leads are coupled to sensors from a remotely housed power supply and logic circuit have exhibited reliability defects stemming from R.F. interference and the like associated with the use of such long cable type interconnections.

Another aspect detracting from the acceptability of typical detection and warning devices stems from the galvanic action induced corrosion of probes which are energized from direct current type power supplies. This electrolytic-type action greatly lowers the lifespan of such probes to the extent that the operational reliability, even of monitoring and alarm devices which normally are not within a liquid environment, is considerably diminished. Further, the design criteria for such devices dictates a simplicity such that unit costs can be achieved in their manufacture permitting wide consumer market acceptance. Where reliability factors additionally must be built into the systems, such cost considerations become difficult to accommodate.

SUMMARY

The present invention is addressed to an apparatus and system serving to reliably monitor given locations for the occurrence of moisture or liquid producing failure. Characterized in exhibiting high reliability, simplicity and ease of use, the apparatus ideally has utility both within consumer as well as industrial markets.

To achieve a necessary simplicity of use, the apparatus is formed having two housings electrically associated by an elongate cable. The first of these housings is designed for mounting at a convenient location, as upon a wall or the like, suited for ease of operator access. Retaining a d.c. power supply such as a battery, along with an alarm device, such as a horn, as well as an activation and test switch, the first housing is positioned to promote periodic testing and battery replenishment by the user. The second housing, much smaller in extent than the first, serves to support the sensing probes of the system and, importantly, the solid state switching components with which the probes operationally perform to generate an alarm output. By so positioning the solid state switching in adjacency with the probes, spurious R.F. type interference phenomena otherwise occasioned with the use of elongate cables are eliminated, while the advantages of providing a conveniently positioned battery power supply, alarm and test system are retained. Preferably, these solid state components, as well as their connections with each of the probes, are provided in a small encapsulatively sealed or "potted" housing. This housing may, for example, be adhesively mounted utilizing convenient tape techniques at the proper location with respect to the site being monitored for moisture or water excursions.

Another feature and object of the invention resides in the provision of a probe structure utilized with the dual housing arrangement which, ideally, is immune from the corrosive galvanic action typically encountered where d.c. probe monitoring techniques are desired. The probes utilized with the apparatus of the instant invention are fabricable at reasonable cost commensurate with the objective of developing an apparatus suited for introduction into the high volume consumer market. These probes are formed having a base component fashioned of a metal characterized in being capable of developing an oxide surface layer which exhibits hardness and immunity to corrosion and serves to isolate the internally disposed portions of metal from the environment initially forming the oxide coating. One surface portion of each probe is fashioned having a noble metal layer such as platinum which is substantially inert to galvanic action and the like and which functions as the conducting component of the probe. The metal oxide surfaces extending beyond the noble metal layer are found to remain substantially immune from the noted electrolytic or galvanic action in the course of use whether in an alarm fashion or where immersion is somewhat extended in such applications as surface measurement or depth control. By utilizing the probe structure of the invention, the highly desired attributes of a noble metal surface may be provided at relatively low cost in consonance with the objects of the invention looking to the production of monitoring units suited for the high volume market. Generally, the noble metal coating, such as platinum, will be deposited upon a base material, such as aluminum, titanium niobium or tantalum, and will exhibit a layer of thickness of about 100 micro inches. Following deposition of the noble metal, the underlying base material is permitted to oxidize in situ to develop the noted hard oxide surface coating representing the remaining surface area of each probe.

Another feature and object of the invention is to provide apparatus of the type described wherein the solid state switching component thereof, which is mounted in the noted second housing, is present as a silicon controled rectifier (SCR). The probe connections with this SCR are with the anode and gate thereof. Adjustment of the relative sensitivity of the switch to electrolytically derived current between the probes is adjusted through the insertion of a resistor or impedance between the noted gate and cathode of the solid state device. Preferably, the entire SCR, as well as its connections with the noble metal surface of each probe and the resistor, are located within the second housing and are encapsulated therewithin through potting procedures.

Other objects of the invention will, in part, be obvious and will, in part, appear hereinafter.

The invention, accordingly, comprises the apparatus possessing the construction, combination of elements and arrangement of parts which are exemplified by the following detailed disclosure. For a fuller understanding of the nature and objects of the invention, reference should be had to the following detailed description taken in connection with the accompanying drawings.

BRIEF DESCRIPTION OF THE DRAWINGS

FIG. 1 is a pictorial representation of an installation of apparatus embodying the concepts of the instant invention;

FIG. 2 is a perspective view of one housing utilized in conjunction with the instant invention;

FIG. 3 is a pictorial representation of a second housing utilized in accordance with the invention;

DETAILED DESCRIPTION

Figure 4:
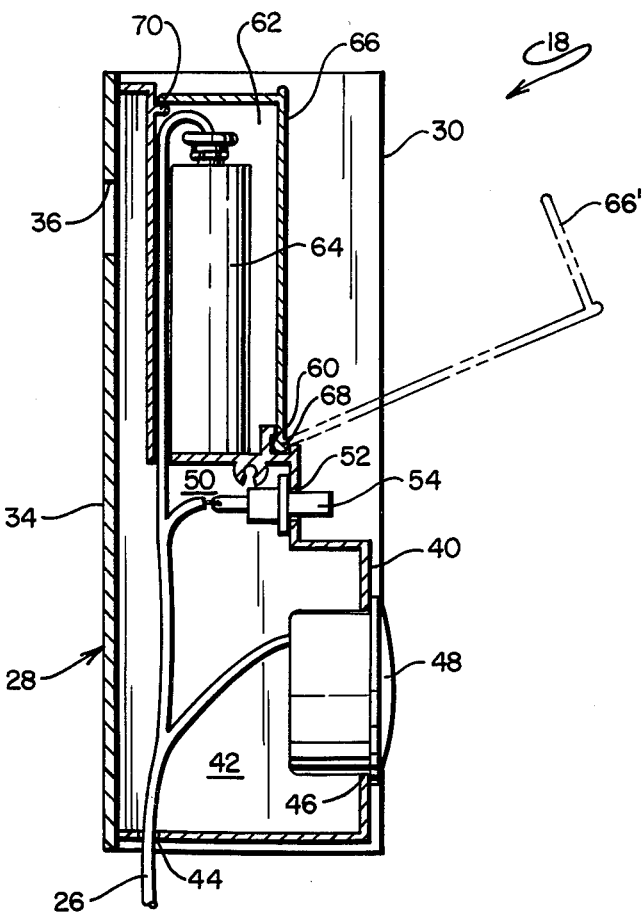
FIG. 4 is a partial sectional view of the housing shown in FIG. 2, taken through the plane 4—4 represented therein.

As noted earlier herein, the apparatus and system of the invention finds utility both in industrial as well as domestic applications. For the latter utility, the inventive arrangement of components derives more reliable performance, in part, in consequence of the positioning of those components requiring periodic maintenance or testing at a location permitting convenient access by the user. For example, FIG. 1 pictorially and schematically illustrates a hot water heater 10 found in typical domestic use. The heater sits upon a cement floor 12 and, usually, near a wall, for example as at 14. Shown positioned upon this wall at 16 is a monitoring and alarm apparatus according to the invention. Apparatus 16 includes a first housing 18 which is positioned upon the wall at an elevation with respect to floor 12 permitting easy access thereto by the home owner for purposes of replenishing battery supplies and carrying out conventional testing procedures. Attached to wall 14 adjacent floor 12 is a second housing 20 from which protrude two conductive probes 22 and 24. Probes 22 and 24 are spaced from the surface of floor 12 but are positioned in close adjacency thereto. Housings 18 and 20 are connected and electrically associated by an elongate flexible cable 26. As will become apparent in the disclosure to follow, the utilization of an elongate cable as at 26 becomes practical by virtue of the relative positioning of logic components within apparatus 16.

Looking to FIGS. 2 and 4, the structure of housing 18 is revealed in detail. Generally, housing 18 is formed of three principal components which advantageously can be fabricated under low tooling cost considerations, for example utilizing aluminum extrusion techniques. The outer component 28 of the housing is shown to comprise a simple channel extrusion. The extrusion at 28 is configured to define two sides 30 and 32 and a back 34 of the housing. Back 34 additionally is configured to retain one or more keyholes 36 (FIG. 4) suited for convenient wall mounting. Also shown in FIG. 2 is one of two self-threading retaining screws 38 which will be observed to interconnect the entire assembly. Screw 38 extends through a bore formed within side 32. A corresponding and symmetrically disposed screw is positioned for insertion through a symmetrically disposed bore within side 30. The second component of the assembly is comprised of an inner housing 40 which is formed, for example, by conventional extrusion procedures and has a width selected for slideable insertion between the inwardly facing surfaces of sides 30 and 32 of outer component 28. As revealed in FIG. 4, when thus positioned within component 28, inner housing 40 defines a lower chamber 42 having one aperture 44 through which cable 26 extends and a second, larger aperture 46 having a diameter for receiving a conventional, electrically energized audible alarm device 48.

Inner housing 40 additionally is configured in stepped-down fashion to define an intermediate chamber 50 having an opening 52 formed therein to receive a three position switch 54. Switch 54 is retained in position by screws as at 56 and 58 extending from the outward surface of inner housing 40 (FIG. 2) Not shown in the drawings are indicia positioned adjacent switch 54 on the outward surface of housing 40 which provide "on" and "off" designations as well as a "test" positional designation. Intermediate chamber 50 additionally is configured having a channel 60 positioned to threadably engage self-threading screws as shown in FIG. 2 at 38. The upwardly disposed portion of inner housing 40 serves to define the rearwardly disposed surface of a chamber 62 suited for retaining a conventional battery 64. Chamber 62 is further established by a battery cover 66, again formed as an extrusion and incorporating an integrally formed bead 68 which is insertable in hinge fashion within a corresponding channel formed within inner housing 40. Cover 66 is retained in its closed orientation by a frictional engagement with a small flange 70 extending from the forwardly facing surface of housing 40 within chamber 62. FIG. 4 also shows that cable 26 provides interconnection between three position switch 54, the electrical terminals of alarm 48 and the terminals of battery 64. As is apparent, the user of the apparatus need only pull battery cover 66 outwardly for access to battery chamber 62. The open position of battery cover 66 is shown in FIG. 4 in phantom at 66'.

Figure 5:
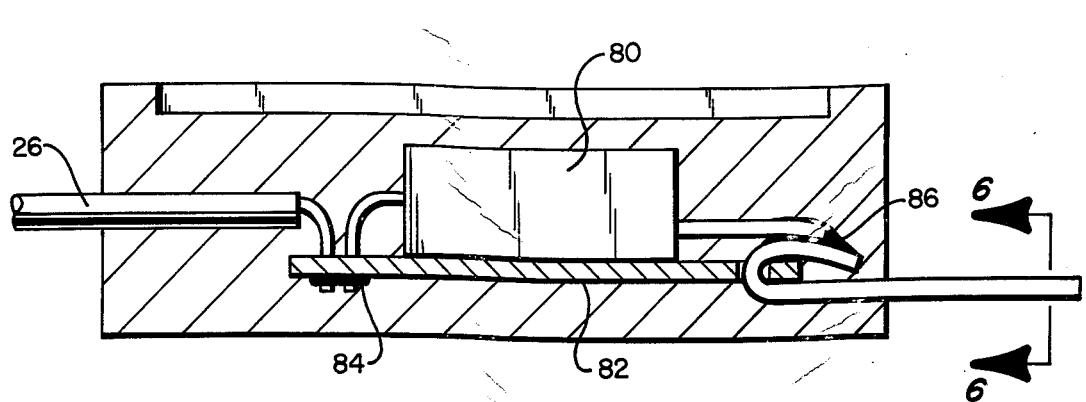
FIG. 5 is a sectional view of the second housing shown in FIG. 3, taken through the plane 5—5 represented therein.

Turning to FIGS. 3 and 5, the second housing 20 of the apparatus 16 is revealed in more detail. Housing 20 is formed of a thermoplastic resin or other suitable plastic utilizing conventional injection molding procedures. As revealed in FIG. 5, the housing serves to encapulate the logic components of the apparatus as well as the connections therewith to cable 26 and probes 22 and 24. In this regard, these components are seen to include a silicon controlled rectifier (SCR) 80 which is mounted upon a conventional circuit board 82. One of the two terminal connections of SCR 80 with cable 26 is shown at 84, while a corresponding terminal connection with probe 22 is revealed at 86. These connections are made prior to the injection molding formation of the housing by soldering or the like. Other modifying components such as resistors or other forms of solid state switching may additionally or in substitution be encapsulated within second housing 20.

Figure 7:
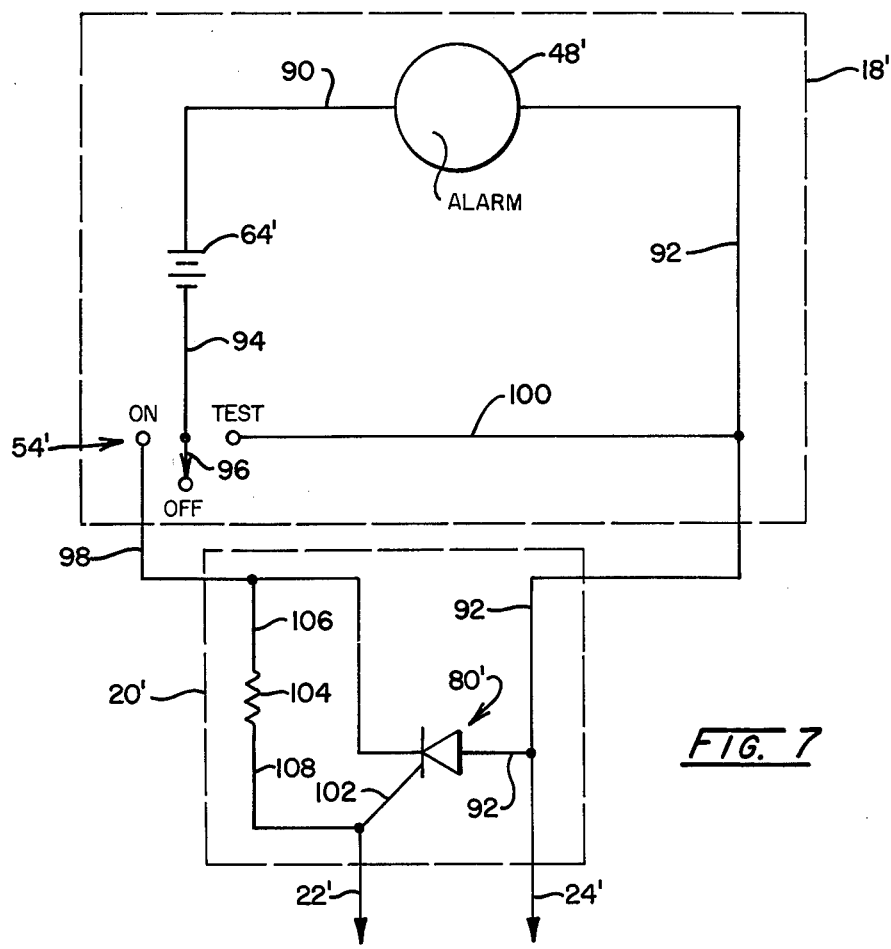
FIG. 7 is a schematic diagram of a circuit utilized in conjunction with the apparatus and system of the invention.

Looking to FIG. 7, a schematic circuit diagram for the apparatus of the invention is revealed. For clarity, alarm 48, switch 54, battery 64, probes 22 and 24 and SCR 80 are represented in FIG. 7 with the same numeration utilized heretofore, but primed. As shown in the drawing, one input to alarm 48' is coupled to the positive terminal of battery 64' from along line 90. The opposite input to alarm 48' is coupled through line 92 to the anode of SCR 80'. Line 92 and the anode of SCR 80' also are coupled to probe 24'. The negative terminal of battery 64' is coupled through line 94 to the common, non-connective terminal of three-way switch 54'. Note that the throw of the switch, designated at numeral 96, is shown in an "off" position. The remaining positions represented in FIG. 7 are designated "on" and "test". The "on" terminal of switch 54' is coupled through line 98 to the cathode of SCR 80', while the "test" terminal is coupled through line 100 to line 92, leading, in turn, to one side of alarm 48'.

Probe 22' of the assembly is connected through line 102 to the gate of SCR 80' and, optionally, may be coupled through an impedance, present as resistor 104, to the cathode of the SCR. In this connection, resistor 104 is shown connected between lines 98 and 102 by respective lines 106 and 108. As is apparent, the presence of the impedance at resistor 104, as compared to the effective impedance exhibited by a given conductive liquid between probes 22' and 24', serves to control the gateability or sensitivity of the solid state switching device 80' by adjusting that bias requisite to gating.

In the interest of further clarity, those components within the schematic circuit of FIG. 7 which are incorporated within housing 18 are surrounded by a dashed boundary 18'. Additionally, those components which are encapsulated, at least in part, within secondary housing 20 are shown surrounded by the dashed boundary 20'. As is apparent, those portions of lines 92 and 98 extant without the boundaries at 18' and 20' are positioned within elongate flexible cable 26. As noted earlier, in consequence of the close adjacency between probes 22' and 24' with the solid state switching, as represented at SCR 80', interference to the switching function occasioned from spurious R.F. signals is eliminated. In consequence, the noted elongate cable 26 is available for use with the apparatus of the invention. Further, the relative remoteness of alarm 48' from the solid state switching function additionally assures no interference to the switching logic at such time as the alarm 48' is activated. As is apparent, the operator manipulates the switch 54' to move the common throw 96 thereof to the "on" terminal for normal operation and to the "test" terminal for energization of alarm 48' through a circuit including lines 92, 100, 94, battery 64' and line 90. Inasmuch as the housing 18 is at a convenient elevation, such testing may be carried out with relative ease and, consequently, with the probability of more frequency.

As noted earlier herein, probes 22 and 24 are configured having a structure assuring their reliability over a relatively extended lifespan of use. Probes formed of conventional conductive materials such as iron, copper, tin, zinc or the like, will rapidly deteriorate due to galvanic or electrolytic-type action to the extent that, under conditions of frequent immersion, their use with apparatus as presently described would become somewhat impractical. Certain metals, for example the noble metals, are relatively immune from these corrosive effects of galvanic activity, for example probes formed of platinum are found to remain adequately conductive for periods of years. The art utilizing immersed probes generally has resorted to carbon structures, however these structures are found to slowly erode in disadvantageous fashion. Of course, the noble metals generally are considered too expensive for use in conventional probe-type monitoring systems.

Figure 6:
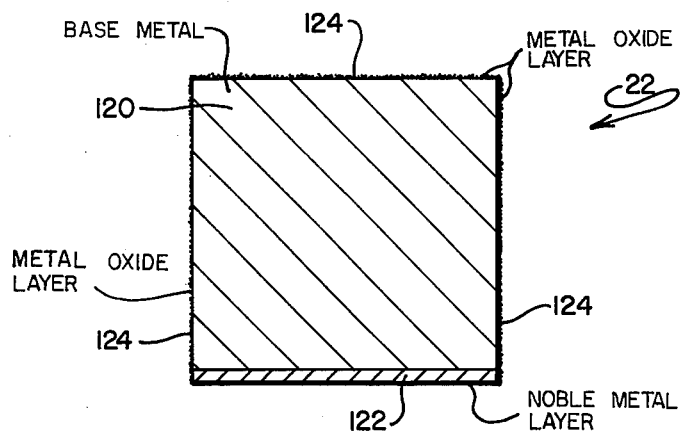
FIG. 6 is a sectional view of a probe shown in FIG. 5 and taken through the plane 6—6 represented in that figure.

Looking to FIG. 6, the cross section, for example, of probe 22 is revealed. Probe 22 is formed of a base material 120 which is a metal selected from the group consisting of titanium, tantalum, niobium and aluminum. These metals have, at times, been designated as "valve" metals and all are observed to quickly form oxides thereof at their surfaces upon exposure to the atmospheric environment or such environments as would serve to promote surface oxide formation. The oxides which are formed are continuous and hard and are observed to adhere with a high degree of adhesion to the base metal upon which they are formed. With the instant invention, a sheet of the material forming base 120, preferably titanium, is coated with a noble metal, preferably platinum, only along one surface thereof. The coating takes place when the surface is clean and free of oxides. This coating or platinization, shown in exaggerated form as layer 122 in FIG. 6, is provided as a very thin layer having a thickness preferably of about 100 micro inches. The coating procedure is conventional, techniques such as electroplating or the like being utilized. Following coating, separate strips are cut from the coated sheet to form probes having the cross sectional configuration shown in FIG. 6. Additionally, rapidly following the severence of these probe strips from the sheet, oxidation of the remaining three surfaces of base material takes place to provide an in situ formation of an oxide layer, as represented in exaggerated fashion at 124. The oxide layer coated surfaces of the probes are found to be substantially inert within the liquid environments to which they may be subjected and the probe, while remaining relatively inexpensive due to the very small amount of platinum metal utilized, is suited for use in a variety of low cost applications as described herein.

Since certain changes may be made in the above apparatus and system without departing from the scope of the invention herein involved, it is intended that all matter contained in the above description or shown in the accompanying drawings shall be interpreted as illustrative and not in a limiting sense.

What is claimed is:

1. Apparatus for detecting the presence of liquid at a given location comprising;
   a first housing mountable at positions remote from said given location;
   alarm means mounted within said first housing and energizable to provide an output signal;
   means within said housing for retaining a d.c. power supply;
   at least two spaced metal probes each said probe comprising;
   a base component formed of a metal selected from the group consisting of aluminum, titanium, niobium and tantalum;
   a noble metal layer intimately adhered to one surface of said base component;
   an oxide of said select metal substantially covering, in situ, the remaining surface portions of said base component;
   solid state switching means electrically coupled with said probes and having an output switching condition when said probes are simultaneously immersed in said liquid;
   a second housing for supporting said probes and said solid state switching means in substantially close adjacency and configured for encapsulatively sealing said switching means from the environment of said liquid means retained within said second housing for electrically coupling said noble metal layer of each said probe with said solid state switching means; and
   flexible cable means connected between said first and second housing means for asserting current from said power supply to said solid state switching means, and for effecting the energization of said alarm means in the presence of said output switching condition.

2. The apparatus of claim 1 in which said solid state switching means is configured having a latching characteristic for effecting a sustained conveyance of current to said alarm means upon an initial said simultaneous contact of said probes with said liquid.

3. The apparatus of claim 1 including manually actuable switch means mounted upon said first housing and having a first switching configuration for enabling said solid state switching means to derive said output switching condition, and a second switching configuration for effecting a direct energization of said alarm means from said power supply, for carrying out operational testing.

4. The apparatus of claim 3 in which said alarm means is configured as an accoustic transducer.

5. The apparatus of claim 1 in which said solid-state switching means is present as a silicon controlled rectifier, the anode of which is electrically coupled to one said probe, the gate of which is electrically coupled to another said probe, and further including impedance means coupled between said gate and the cathode thereof having an impedance value selected for enhancing the gating sensitivity of said rectifier to respond to the said simultaneous immersion of said probes.

6. The apparatus of claim 1 in which said noble metal is platinum.

7. The apparatus of claim 1 in which said base component select metal is titanium and said noble metal is platinum having a thickness of about 100 micro inches.

8. The apparatus of claim 1 in which said solid state switching means is configured having a latching characteristic for effecting a sustained conveyance of current to said alarm means upon an initial said simultaneous contact of said probes with said liquid.

9. The apparatus of claim 1 including manually actuable switch means mounted upon said first housing and having a first switching configuration for enabling said solid state switching means to derive said output switching condition and a second switching configuration for effecting a direct energization of said alarm means from said power supply for carrying out operational testing.

10. The apparatus of claim 9 in which said solid state switching means is present as a silicon controlled rectifier, the anode of which is electrically coupled to one said probe, the gate of which is electrically coupled to another said probe, and further including impedance means coupled between said gate and the cathode thereof having an impedance value selected for enhancing the gating sensitivity of said rectifier to respond to the said simultaneous immersion of said probes.

11. The apparatus of claim 10 in which said alarm means is configured as an accoustic transducer.

12. The apparatus of claim 10 including means retained within said second housing for electrically coupling said noble metal layer of each said probe with said solid state switching means.

13. In a liquid level responsive system of a variety wherein at least two conductive probes are utilized which, upon being simultaneously positioned in contact with a conductive liquid, serve to complete a d.c. electrical circuit path through electrical leads to circuit components developing an output signal, the improvement wherein each of said probes comprises:
   a base component formed of a metal selected from the group consisting of: aluminum, tantalum, niobium and titanium and having first and second surface portions;
   a noble metal layer intimately and substantially uniformly adhered to said first surface portion;
   said second surface portion comprising an in situ covering of oxide of said metal of said base component; and
   means electrically coupling said noble metal layer with a said lead.

14. The improved system of claim 13 in which:
   each said probe is elongate in form and exhibits substantially flat surfaces defining a substantially rectangular cross sectional configuration; and
   said noble metal layer is intimately adhered to only one said flat surface.

15. The improved system of claim 14 in which said noble metal is platinum.

16. The improved system of claim 15 in which said base component metal is titanium.

* * * * *